United States Patent
Cao et al.

(10) Patent No.: US 11,114,425 B2
(45) Date of Patent: Sep. 7, 2021

(54) PACKAGING OF RADIATION DETECTORS IN AN IMAGE SENSOR

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN); Chongshen Song, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 16/919,511

(22) Filed: Jul. 2, 2020

(65) Prior Publication Data
US 2020/0335485 A1  Oct. 22, 2020

Related U.S. Application Data

(63) Continuation of application No. PCT/CN2018/074049, filed on Jan. 24, 2018.

(51) Int. Cl.
*H01L 27/146* (2006.01)
*H01L 25/16* (2006.01)
(Continued)

(52) U.S. Cl.
CPC .............. *H01L 25/167* (2013.01); *A61B 6/14* (2013.01); *A61B 6/4007* (2013.01); *G01N 23/046* (2013.01); *G01N 23/10* (2013.01); *G01N 23/18* (2013.01); *G01N 23/203* (2013.01); *G01T 1/24* (2013.01); *H01L 25/162* (2013.01); *H01R 12/52* (2013.01); *H01R 12/716* (2013.01); *H01R 12/718* (2013.01); *A61B 6/502* (2013.01); *G01N 23/20091* (2013.01); *G01N 23/2252* (2013.01); *G01N 2223/629* (2013.01); *G01N 2223/646* (2013.01)

(58) Field of Classification Search
CPC ............ H01L 27/14634; A61B 6/4283; A61B 6/4417; A61B 6/4429; A61B 6/4208; A61B 6/417
See application file for complete search history.

(56) References Cited

U.S. PATENT DOCUMENTS

| 2001/0012412 A1* | 8/2001 | Schulman ............ H04N 5/2253 382/312 |
| 2003/0155516 A1 | 8/2003 | Spartiotis et al. |

(Continued)

FOREIGN PATENT DOCUMENTS

| EP | 1389876 A1 | 2/2004 |
| GB | 2315157 B | 9/1998 |

(Continued)

OTHER PUBLICATIONS

PCT/CN2018/074049 ISA210 PCT ISR Mail Date Oct 24, 2018.

*Primary Examiner* — Don K Wong

(57) ABSTRACT

Disclosed herein is an image sensor comprising: a first package comprising a plurality of radiation detectors mounted on a printed circuit board (PCB); wherein a dead zone of the first package does not extend between neighboring radiation detectors among the plurality of radiation detectors; wherein the radiation detectors have no guard rings or sidewall doping.

26 Claims, 20 Drawing Sheets

(51) Int. Cl.
*A61B 6/14* (2006.01)
*A61B 6/00* (2006.01)
*G01N 23/046* (2018.01)
*G01N 23/10* (2018.01)
*G01N 23/18* (2018.01)
*G01N 23/203* (2006.01)
*G01T 1/24* (2006.01)
*H01R 12/52* (2011.01)
*H01R 12/71* (2011.01)
*G01N 23/20091* (2018.01)
*G01N 23/2252* (2018.01)

(56) References Cited

U.S. PATENT DOCUMENTS

| | | | |
|---|---|---|---|
| 2004/0200971 | A1 | 10/2004 | De Keyser |
| 2006/0238631 | A1* | 10/2006 | Ligozat ............... H04N 5/3694 |
| | | | 348/294 |
| 2008/0093560 | A1 | 4/2008 | Puhakka et al. |
| 2014/0284752 | A1* | 9/2014 | Kalliopuska ........ H01L 27/1469 |
| | | | 257/448 |

FOREIGN PATENT DOCUMENTS

| | | | |
|---|---|---|---|
| WO | 0065376 | A1 | 11/2000 |
| WO | 2016161542 | A1 | 10/2016 |
| WO | 2016180382 | A1 | 11/2016 |

* cited by examiner

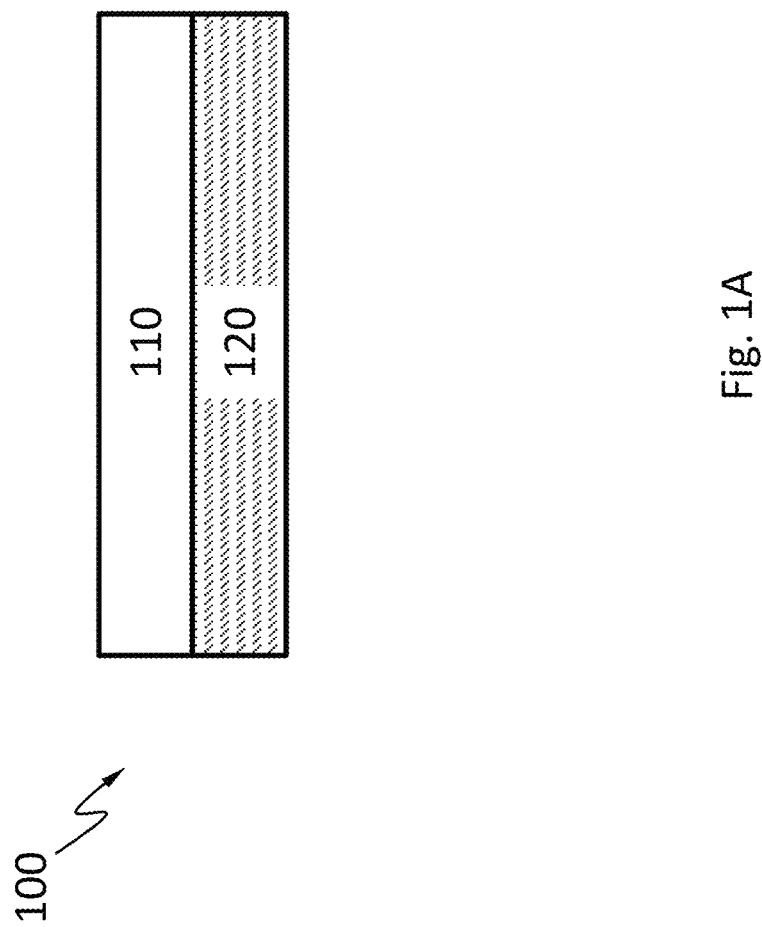

PACKAGING OF RADIATION DETECTORS IN AN IMAGE SENSOR

TECHNICAL FIELD

The disclosure herein relates to radiation detectors, particularly relates to packaging of radiation detectors.

BACKGROUND

A radiation detector is a device that measures a property of a radiation. Examples of the property may include a spatial distribution of the intensity, phase, and polarization of the radiation. The radiation may be one that has interacted with a subject. For example, the radiation measured by the radiation detector may be a radiation that has penetrated or reflected from the subject. The radiation may be an electromagnetic radiation such as infrared light, visible light, ultraviolet light, X-ray or γ-ray. The radiation may be of other types such as α-rays and β-rays.

One type of radiation detectors is based on interaction between the radiation and a semiconductor. For example, a radiation detector of this type may have a semiconductor layer that absorbs the radiation and generate charge carriers (e.g., electrons and holes) and circuitry for detecting the charge carriers.

SUMMARY

Disclosed herein is an image sensor comprising: a first package comprising a plurality of radiation detectors mounted on a printed circuit board (PCB); wherein a dead zone of the first package does not extend between neighboring radiation detectors among the plurality of radiation detectors; wherein the radiation detectors have no guard rings or sidewall doping.

According to an embodiment, the first package is mounted on a system PCB by a plug and a receptacle.

According to an embodiment, the first package is tilted relative to the system PCB.

According to an embodiment, the first package is mounted on a system PCB by wire bonding.

According to an embodiment, the image sensor further comprises a second package, wherein the dead zone of the first package is shadowed by the second package.

According to an embodiment, the dead zone of the first package is shadowed by an active area of the second package.

According to an embodiment, the first package is rectangular in shape.

According to an embodiment, the first package is hexagonal in shape.

According to an embodiment, a gap between two neighboring radiation detectors is not wider than a pixel of the two neighboring radiation detectors.

According to an embodiment at least one radiation detector of the radiation detectors does not comprise a perimeter zone along at least three sides of the at least one radiation detector.

According to an embodiment, at least one of the radiation detector packages comprises a radiation absorption layer and an electronics layer; wherein the radiation absorption layer comprises an electrode; wherein the electronics layer comprises an electronics system; wherein the electronics system comprises: a first voltage comparator configured to compare a voltage of the electrode to a first threshold; a second voltage comparator configured to compare the voltage to a second threshold; a counter configured to register a number of radiation particles reaching the radiation absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the electronics system further comprises a capacitor module electrically connected to the electrode, wherein the capacitor module is configured to collect charge carriers from the electrode.

According to an embodiment, the controller is configured to activate the second voltage comparator at a beginning or expiration of the time delay.

According to an embodiment, the electronics system further comprises a voltmeter, wherein the controller is configured to cause the voltmeter to measure the voltage upon expiration of the time delay.

According to an embodiment, the controller is configured to determine a radiation particle energy based on a value of the voltage measured upon expiration of the time delay.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

Disclosed herein is a system comprising the image sensor disclosed herein and a radiation source, wherein the system is configured to perform radiography on human chest or abdomen.

Disclosed herein is a system comprising the image sensor disclosed herein and a radiation source, wherein the system is configured to perform radiography on human mouth.

Disclosed herein is a cargo scanning or non-intrusive inspection (NII) system, comprising the image sensor disclosed herein and a radiation source, wherein the cargo scanning or non-intrusive inspection (NII) system is configured to form an image using backscattered radiation.

Disclosed herein is a cargo scanning or non-intrusive inspection (NII) system, comprising the image sensor disclosed herein and a radiation source, wherein the cargo scanning or non-intrusive inspection (NII) system is configured to form an image using radiation transmitted through an object inspected.

Disclosed herein is a full-body scanner system comprising the image sensor disclosed herein and a radiation source.

Disclosed herein is a radiation computed tomography (Radiation CT) system comprising the image sensor disclosed herein and a radiation source.

Disclosed herein is an electron microscope comprising the image sensor disclosed herein, an electron source and an electronic optical system.

Disclosed herein is a system comprising the image sensor disclosed herein, wherein the system is a radiation telescope, or a radiation microscopy, or wherein the system is configured to perform mammography, industrial defect detection, microradiography, casting inspection, weld inspection, or digital subtraction angiography.

BRIEF DESCRIPTION OF FIGURES

FIG. 1A schematically shows a cross-sectional view of a radiation detector, according to an embodiment.

DETAILED DESCRIPTION

FIG. 1A schematically shows a cross-sectional view of a radiation detector 100, according to an embodiment. The radiation detector 100 may include a radiation absorption layer 110 and an electronics layer 120 (e.g., an ASIC) for processing or analyzing electrical signals incident radiation generates in the radiation absorption layer 110. In an embodiment, the radiation detector 100 does not comprise a scintillator. The radiation absorption layer 110 may include a semiconductor material such as, silicon, germanium, GaAs, CdTe, CdZnTe, or a combination thereof. The semiconductor may have a high mass attenuation coefficient for the radiation energy of interest.

Figure 1B:
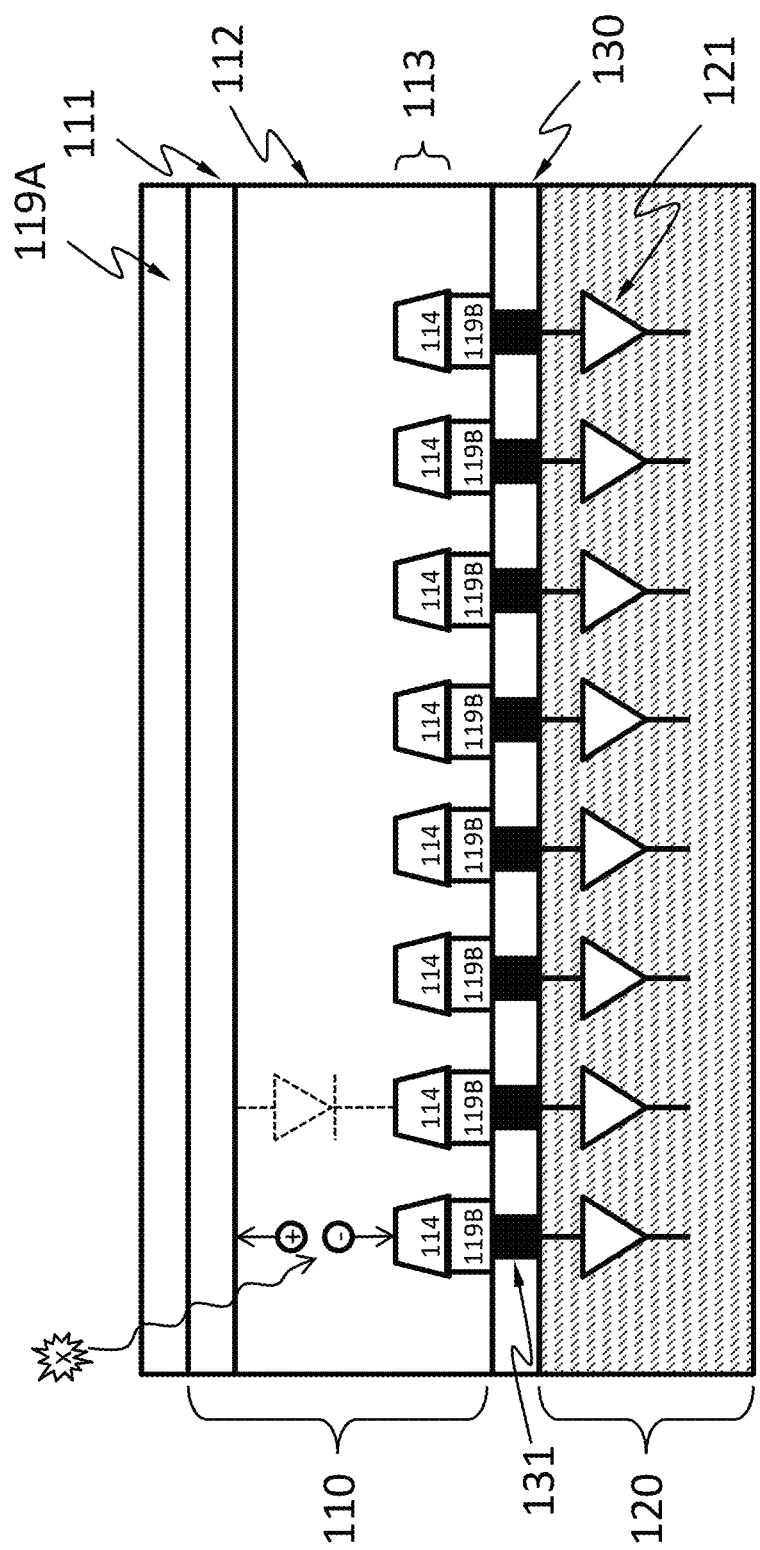
FIG. 1B schematically shows a detailed cross-sectional view of the radiation detector, according to an embodiment.

As shown in a detailed cross-sectional view of the radiation detector 100 in FIG. 1B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1B, each of the discrete regions 114 of the second doped region 113 forms a diode with the first doped region 111 and the optional intrinsic region 112. Namely, in the example in FIG. 1B, the radiation absorption layer 110 has a plurality of diodes having the first doped region 111 as a shared electrode. The first doped region 111 may also have discrete regions.

When a radiation particle hits the radiation absorption layer 110 including diodes, the radiation particle may be absorbed by the radiation absorption layer 110, and one or more charge carriers may be generated in the radiation absorption layer 110 by a number of mechanisms. A radiation particle may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single radiation particle are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a radiation particle incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a radiation particle incident therein flow to the discrete region 114. Namely, less than 2%, less than 1%, less than 0.1%, or less than 0.01% of these charge carriers flow beyond the pixel.

Figure 1C:
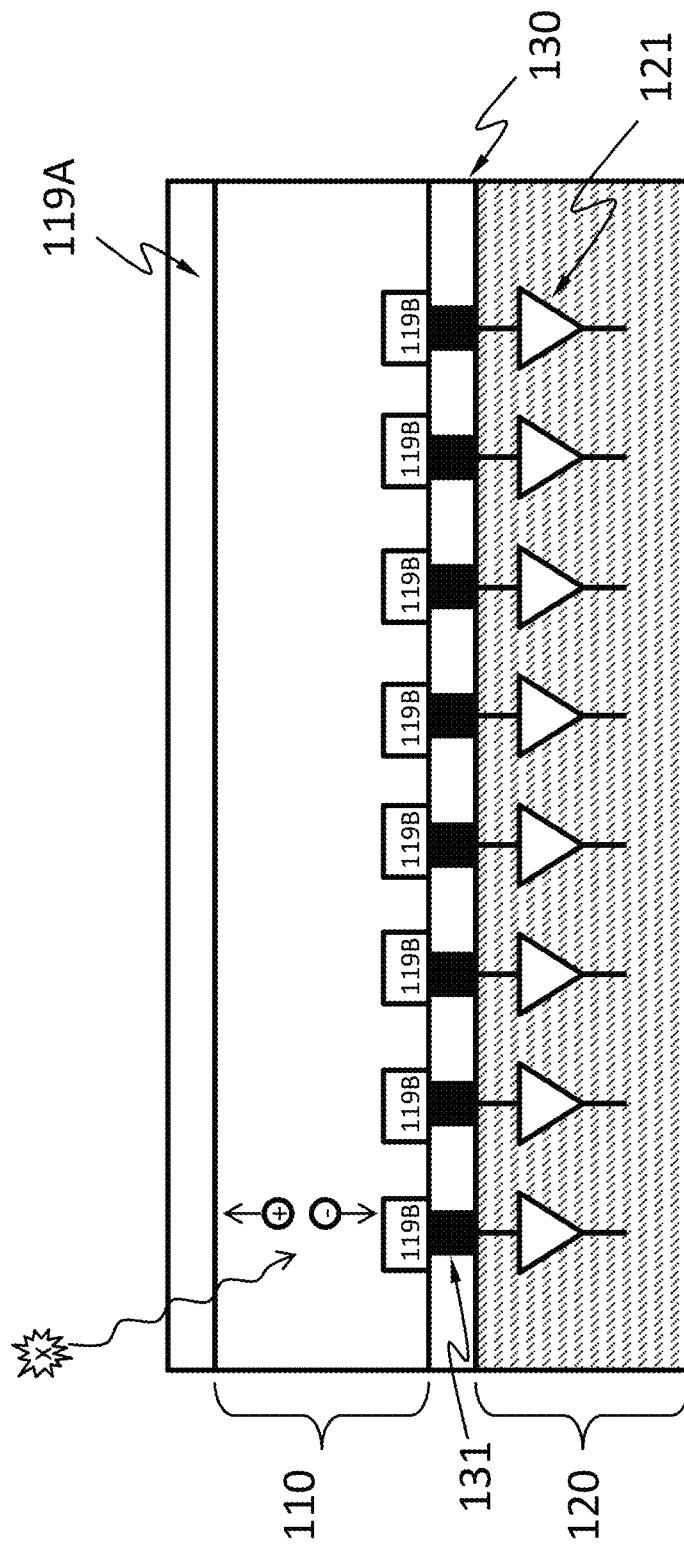
FIG. 1C schematically shows an alternative detailed cross-sectional view of the radiation detector, according to an embodiment.

As shown in an alternative detailed cross-sectional view of the radiation detector 100 in FIG. 1C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation energy of interest.

When a radiation particle hits the radiation absorption layer 110 including a resistor but not diodes, it may be absorbed by the radiation absorption layer 110, and one or more charge carriers may be generated in the radiation absorption layer 110 by a number of mechanisms. A radiation particle may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single radiation particle are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a radiation particle incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a radiation particle incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by radiation particles incident on the radiation absorption layer 110. The electronic system 121 may include an analog circuitry such as a filter network, amplifiers, integrators, and comparators, or a digital circuitry such as a microprocessor, and a memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 2:
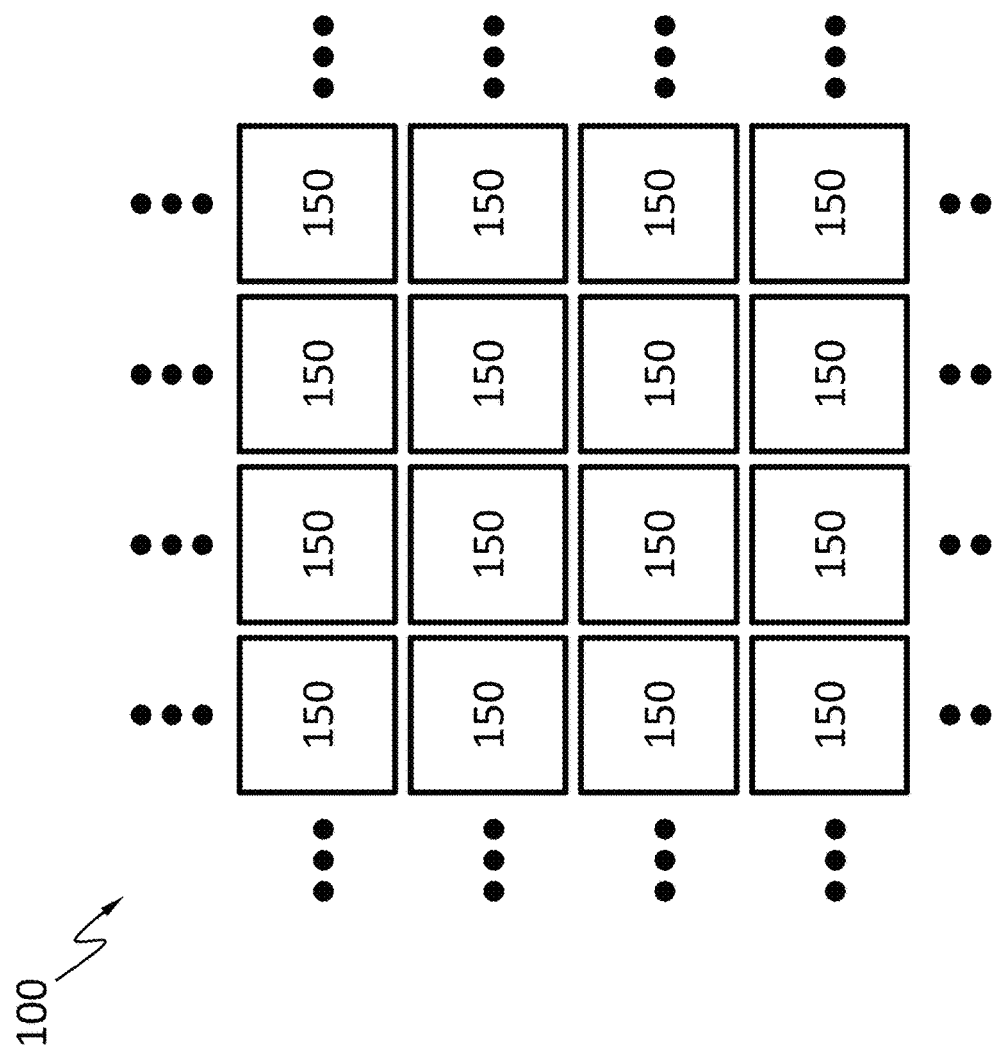
FIG. 2 schematically shows that the radiation detector may have an array of pixels, according to an embodiment.

FIG. 2 schematically shows that the radiation detector 100 may have an array of pixels 150, according to an embodiment. The array may be a rectangular array, a honeycomb array, a hexagonal array or any other suitable array. Each pixel 150 may be configured to detect a radiation particle incident thereon, measure the energy of the radiation particle, or both. For example, each pixel 150 may be configured to count numbers of radiation particles incident thereon whose energy falls in a plurality of bins, within a period of time. All the pixels 150 may be configured to count the numbers of radiation particles incident thereon within a plurality of bins of energy within the same period of time. Each pixel 150 may have its own analog-to-digital converter (ADC) configured to digitize an analog signal representing the energy of an incident radiation particle into a digital signal. The ADC may have a resolution of 10 bits or higher. Each pixel 150 may be configured to measure its dark current, such as before or concurrently with each radiation particle incident thereon. Each pixel 150 may be configured to deduct the contribution of the dark current from the energy of the radiation particle incident thereon. The pixels 150 may be configured to operate in parallel. For example, when one pixel 150 measures an incident radiation particle, another pixel 150 may be waiting for a radiation particle to arrive. The pixels 150 may be but do not have to be individually addressable. The radiation detector 100 may not have guard rings encompassing the pixels 150. The radiation detector 100 may not have sidewall doping that is configured to reduce leakage current on the sidewall of the radiation absorption layer 110.

Figure 3:
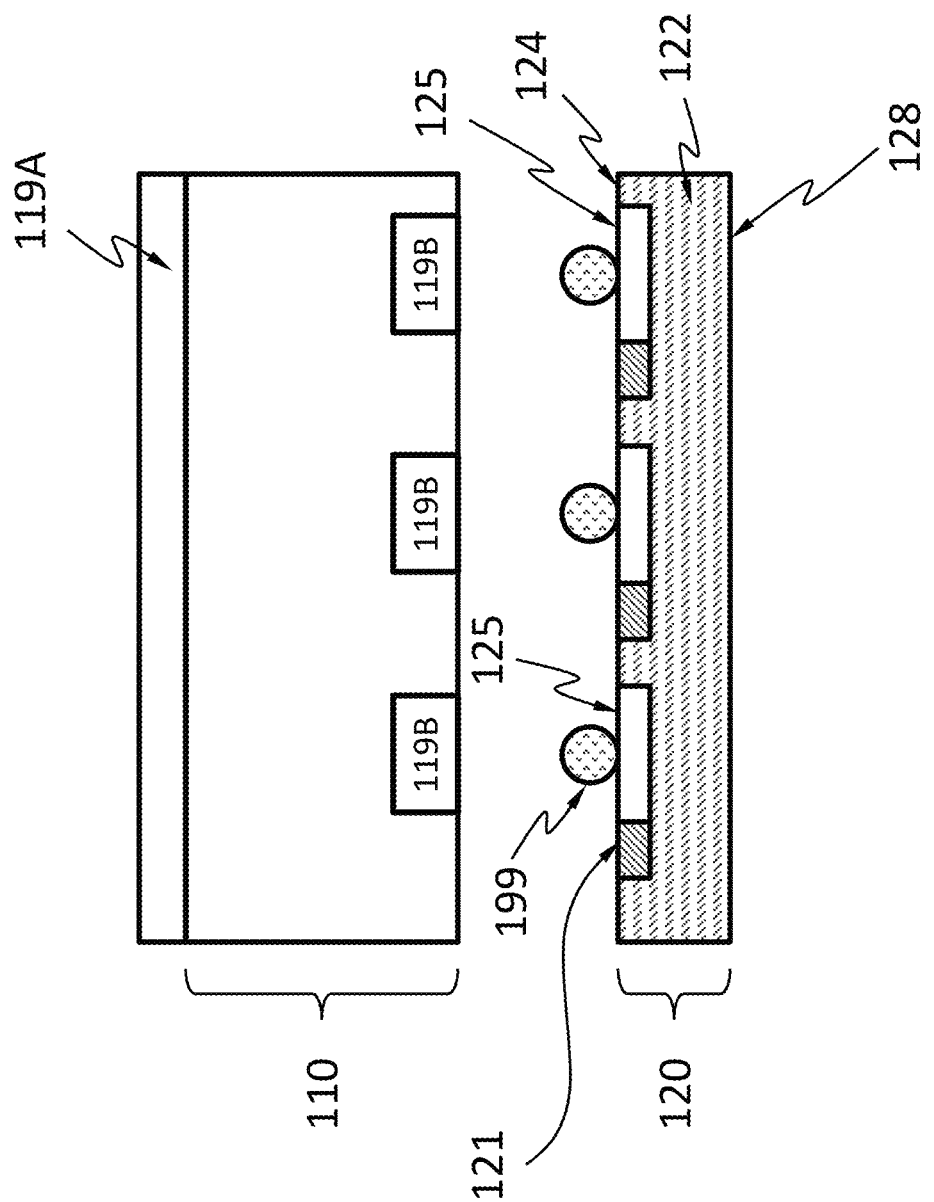
FIG. 3 schematically shows a cross-sectional view of an electronics layer in the radiation detector, according to an embodiment.

FIG. 3 schematically shows the electronics layer 120, according to an embodiment. The electronics layer 120 comprises a substrate 122 having a first surface 124 and a second surface 128. A "surface" as used herein is not necessarily exposed, but can be buried wholly or partially. The electronics layer 120 comprises one or more electric contacts 125 on the first surface 124. The one or more electric contacts 125 may be configured to be electrically connected to one or more electrical contacts 119B of the radiation absorption layer 110. The electronics system 121 may be in or on the substrate 122.

The substrate 122 may be a thinned substrate. For example, the substrate may have at thickness of 750 microns or less, 200 microns or less, 100 microns or less, 50 microns or less, 20 microns or less, or 5 microns or less. The substrate 122 may be a silicon substrate or a substrate or other suitable semiconductor or insulator. The substrate 122 may be produced by grinding a thicker substrate to a desired thickness.

The one or more electric contacts 125 may be a layer of metal or doped semiconductor. For example, the electric contacts 125 may be gold, copper, platinum, palladium, doped silicon, etc.

FIG. 3 schematically shows bonding between the radiation absorption layer 110 and the electronics layer 120 at the electrical contact 119B of the radiation absorption layer 110 and electrical contacts 125 of the electronics layer 120. The bonding may be by a suitable technique such as direct bonding or flip chip bonding.

Direct bonding is a wafer bonding process without any additional intermediate layers (e.g., solder bumps). The bonding process is based on chemical bonds between two surfaces. Direct bonding may be at elevated temperature but not necessarily so.

Flip chip bonding uses solder bumps 199 deposited onto contact pads (e.g., the electrical contact 119B of the radiation absorption layer 110 or the electrical contacts 125). Either the radiation absorption layer 110 or the electronics layer 120 is flipped over and the electrical contact 119B of the radiation absorption layer 110 are aligned to the electrical contacts 125. The solder bumps 199 may be melted to solder the electrical contact 119B and the electrical contacts 125 together. Any void space among the solder bumps 199 may be filled with an insulating material.

Figure 4A:
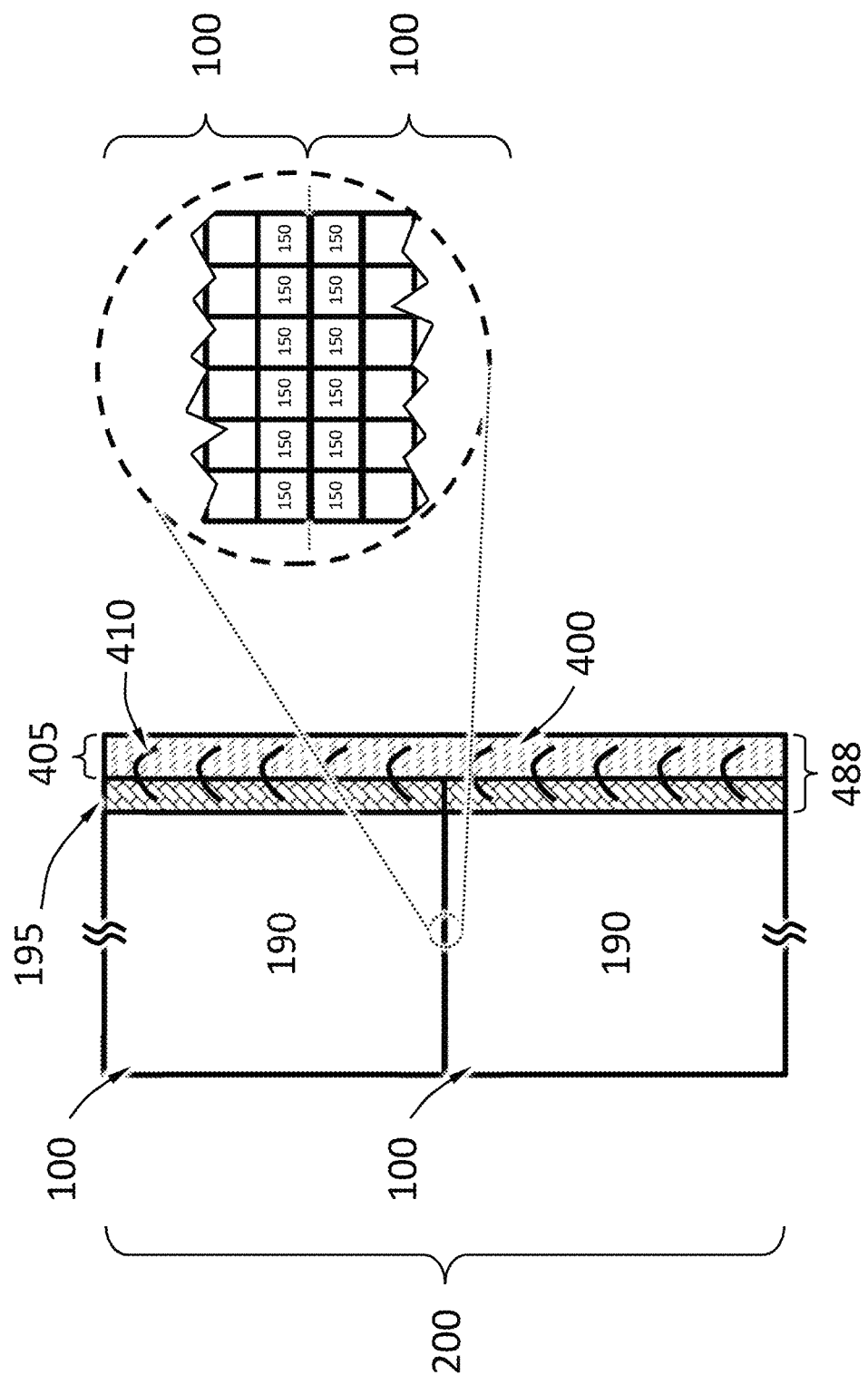
FIG. 4A schematically shows a top view of a package comprising a radiation detector and a printed circuit board (PCB).

FIG. 4A schematically shows a top view of a package 200 including the radiation detector 100 and a printed circuit board (PCB) 400, according to an embodiment. The term "PCB" as used herein is not limited to a particular material. For example, a PCB may include a semiconductor. The radiation detector 100 is mounted to the PCB 400. The PCB 400 may have multiple radiation detectors 100. The PCB 400 may have an area 405 not covered by the radiation detectors 100, for accommodating bonding wires 410. The radiation detector 100 may have an active area 190, which is where the pixels 150 are located. According to an embodiment, at least one of the radiation detectors 100 has the its active area 190 extending to the edges of at least 3 sides of the radiation detector 100. Namely, at least one of the radiation detectors 100 does not comprise a perimeter zone on these sides of that radiation detector 100. A perimeter zone 195 is a zone of the radiation detector 100 that does not detect radiation particles. One side of that radiation detector 100 may have a perimeter zone 195 to accommodate bonding wires 410.

Radiation incident on the perimeter zones 195 of the radiation detectors 100, or on the area 405 of the PCB 400 cannot be detected by the package 200. A dead zone 488 of a package (e.g., package 200) is defined as the area of the radiation-receiving surface of the package, in which incident radiation particles cannot be detected by the radiation detectors in the package. In this example shown in FIG. 4A, the dead zone 488 of the package 200 includes the perimeter zones 195 and the area 405. The dead zone 488 of the package 200 does not extend between neighboring radiation detectors among the multiple radiation detectors 100 of the package 200. For example, as shown in FIG. 4A, any gap between two neighboring radiation detectors is not wider than a pixel of the two neighboring radiation detectors.

Figure 4B:
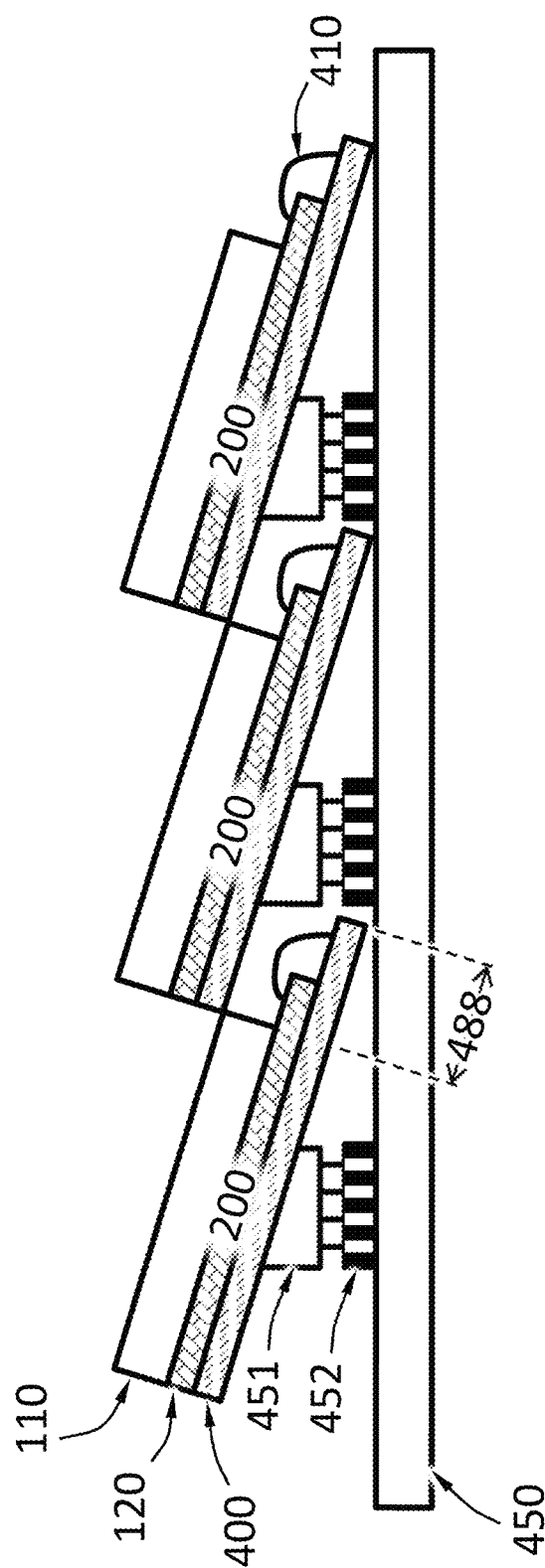
FIG. 4B and FIG. 4C each schematically show a cross-sectional view of an image sensor, where a plurality of the packages of FIG. 4A are mounted to a system PCB.
Figure 4C:
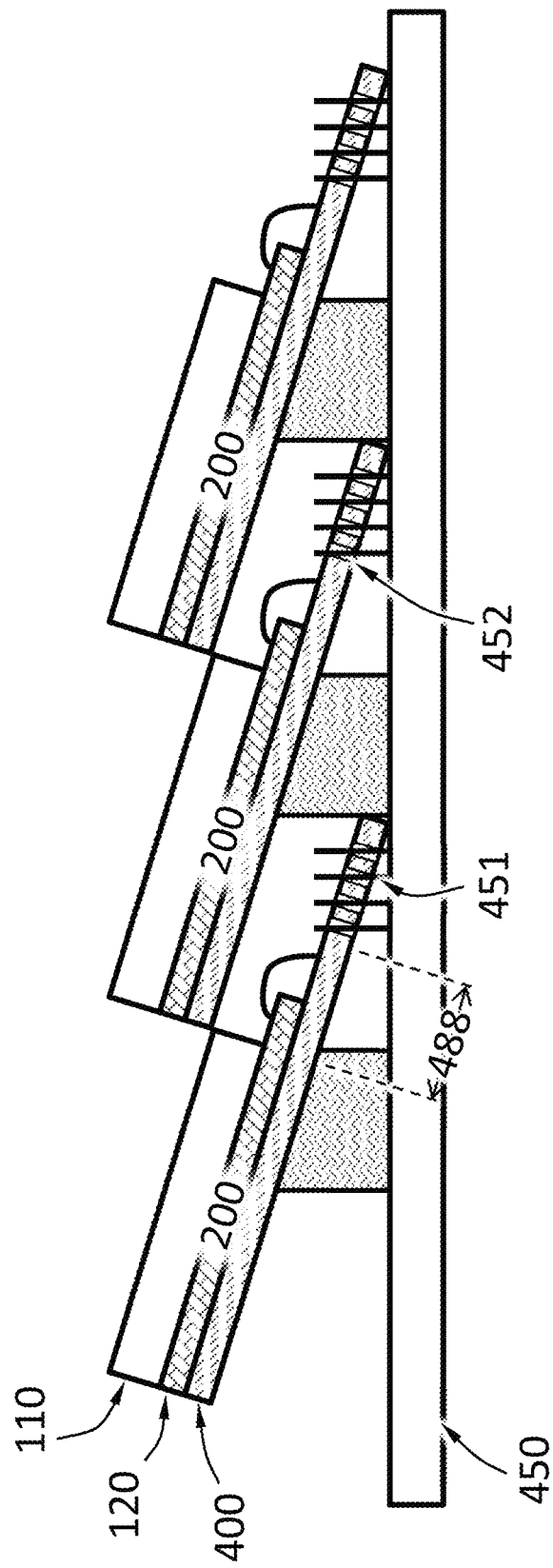

FIG. 4B and FIG. 4C each schematically show that the radiation that would otherwise be incident in the dead zone 488 of the package 200 may be detected by another package whose active area shadows the dead zone 488, according to an embodiment. Multiple the packages 200 may be arranged such that they are tilted relative to a system PCB 450. The dead zone 488 of one package 200 is tucked under a neighboring package such that the dead zone 488 is shadowed by an active area of the neighboring package. The package 200 and its one or more neighboring packages may be arranged very close to each other such that the entirety of the dead zone 488 of the package 200 is shadowed by the one or more neighboring packages. FIG. 4B and FIG. 4C also show the package 200 may be mounted (electrically and mechanically) to the system PCB 450 is by a plug 451 and a receptacle 452. The plug 451 may be part of the PCB 400 and the receptacle 452 may be part of the system PCB 450 (as shown in FIG. 4B), or vice versa (as shown in FIG. 4C). The receptacle 452 may be holes through the system PCB 450 or the PCB 400 for receiving solder.

Figure 5B:
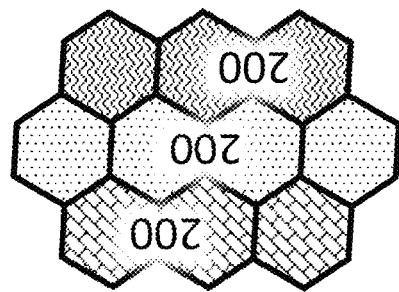
FIG. 5A and FIG. 5B schematically show a large area arrangement of packages of FIG. 4A in an image sensor, according to an embodiment.
Figure 5A:
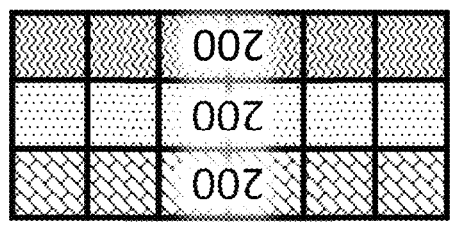

FIG. 5A and FIG. 5B schematically show large area arrangements of packages 200 in an image sensor, according to an embodiment. In this embodiment, the packages 200 may be mounted to a system PCB 450 by plugs and receptacles. The packages 200 may be rectangular in shape, as shown in FIG. 5A, or may be hexagonal in shape, as shown in FIG. 5B. The dead zone of one package is shadowed by an active area of one or more neighboring packages. The gaps between the packages may be negligible in imaging using the image sensor.

Figure 6A:
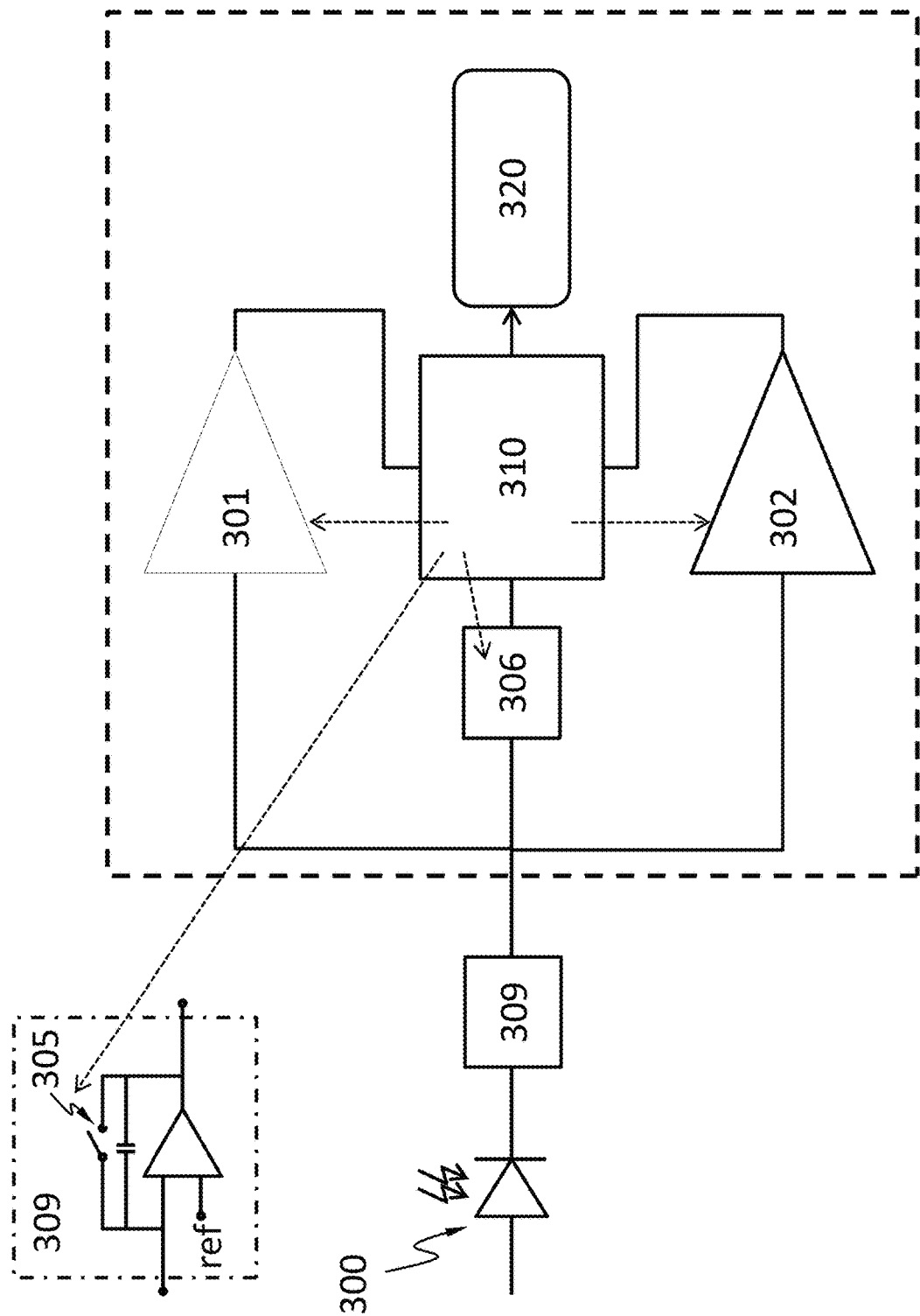
FIG. 6A and FIG. 6B each show a component diagram of an electronic system of the radiation detector in FIG. 1B or FIG. 1C, according to an embodiment.
Figure 6B:
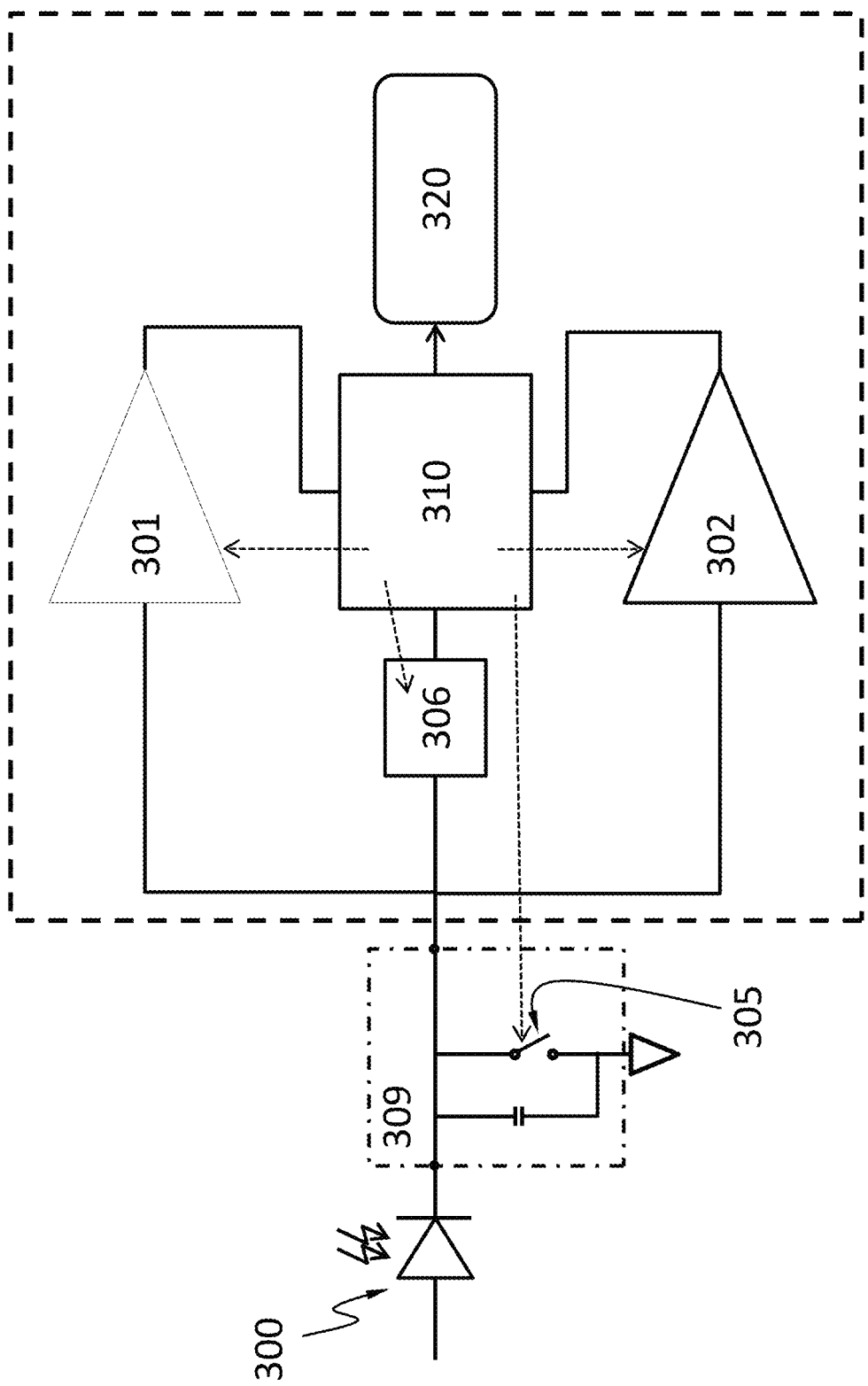

FIG. 6A and FIG. 6B each show a component diagram of the electronic system 121 of the radiation detector 100, according to an embodiment. The electronic system 121 may include a first voltage comparator 301, a second voltage comparator 302, a counter 320, a switch 305, a voltmeter 306 and a controller 310.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident radiation particle. The first voltage comparator 301 configured as a continuous comparator is especially suitable when the incident radiation intensity is relatively high. The first voltage comparator 301 may be a clocked comparator, which has the benefit of lower power consumption. The first voltage comparator 301 configured as a clocked comparator may cause the system 121 to miss signals generated by some incident radiation particles. When the incident radiation intensity is low, the chance of missing an incident radiation particle is low because the time interval between two successive photons is relatively long. Therefore, the first voltage comparator 301 configured as a clocked comparator is especially suitable when the incident radiation intensity is relatively low. The first threshold may be 5-10%, 10%-20%, 20-30%, 30-40% or 40-50% of the maximum voltage one incident radiation particle may generate in the diode or the resistor. The maximum voltage may depend on the energy of the incident radiation particle (i.e., the wavelength of the incident radiation), the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. The second threshold may be at least 50% of the maximum voltage one incident radiation particle may generate in the diode or resistor. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident radiation. However, having a high speed is often at the cost of power consumption.

The counter 320 is configured to register a number of radiation particles reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 7:
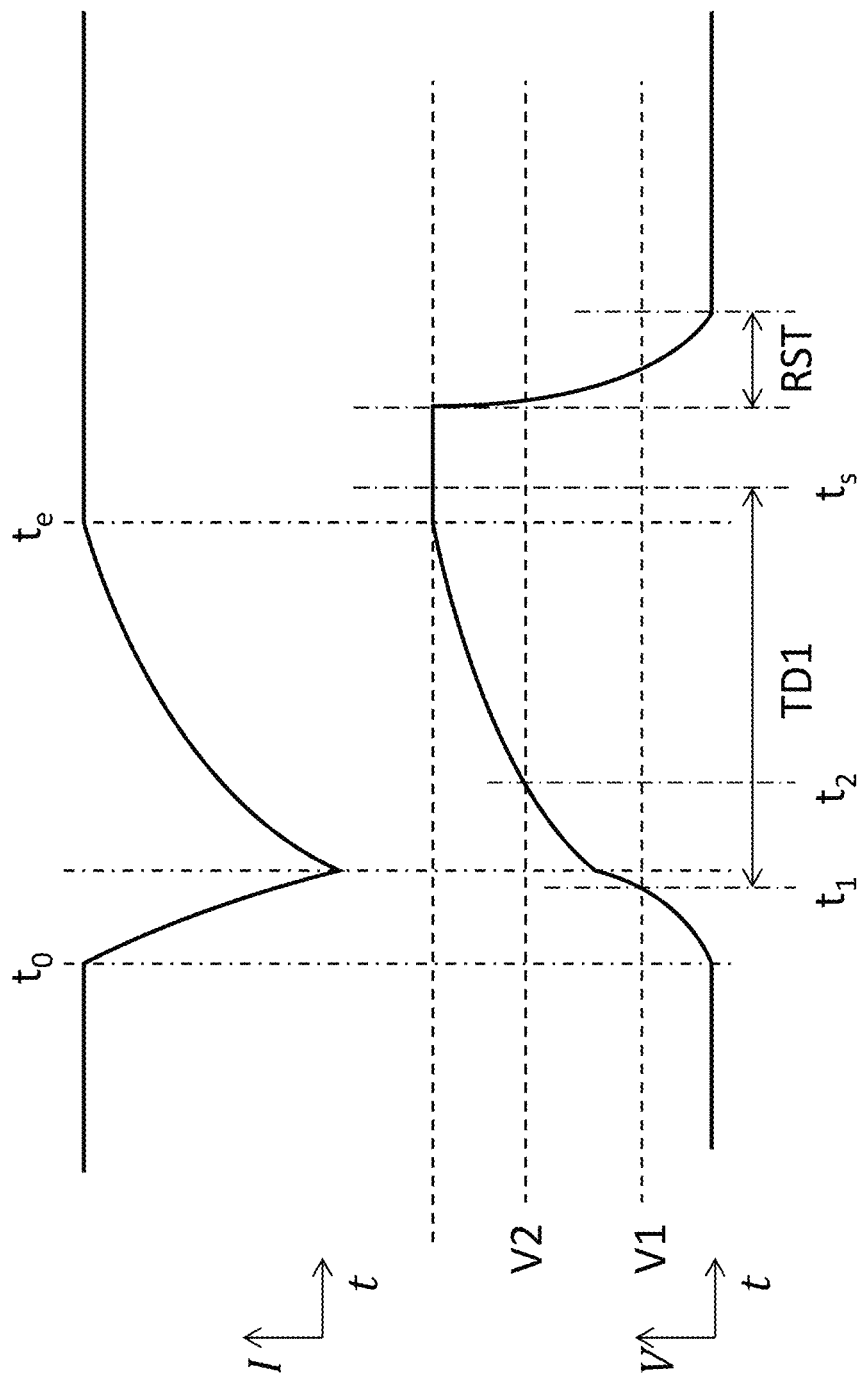
FIG. 7 schematically shows a temporal change of the electric current flowing through an electrode (upper curve) of a diode or an electrical contact of a resistor of a radiation absorption layer exposed to radiation, the electric current caused by charge carriers generated by a radiation particle incident on the radiation absorption layer, and a corresponding temporal change of the voltage of the electrode (lower curve), according to an embodiment.
Figure 8:
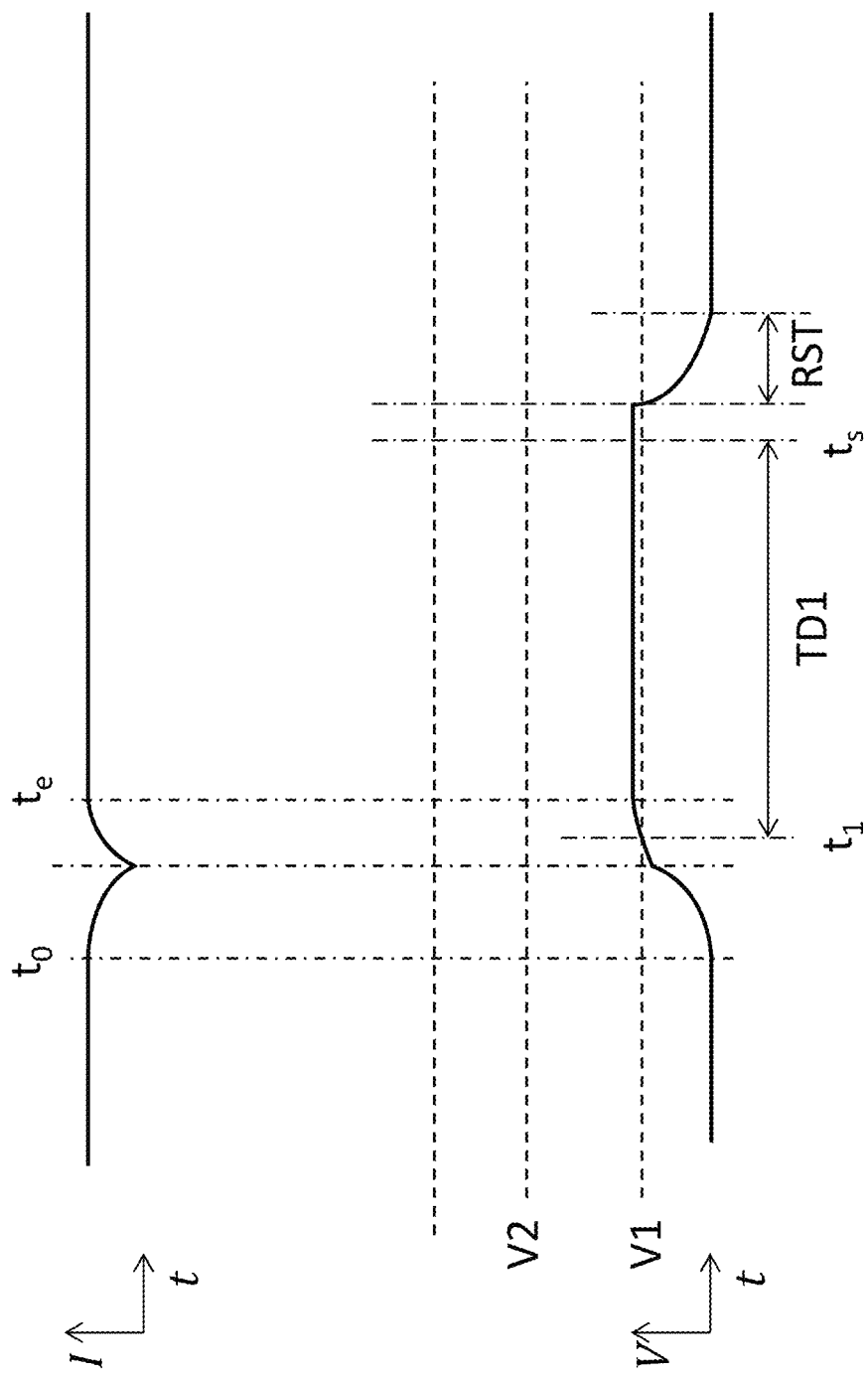
FIG. 8 schematically shows a temporal change of the electric current flowing through the electrode (upper curve) caused by noise (e.g., dark current), and a corresponding temporal change of the voltage of the electrode (lower curve), in the electronic system operating in the way shown in FIG. 7, according to an embodiment.

The system 121 may include a capacitor module 309 electrically connected to the electrode of the diode 300 or which electrical contact, wherein the capacitor module is configured to collect charge carriers from the electrode. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 7, between $t_0$ to $t_1$, or $t_1$-$t_2$). After the integration period has expired, the capacitor voltage is sampled and then reset by a reset switch. The capacitor module can include a capacitor directly connected to the electrode.

FIG. 7 schematically shows a temporal change of the electric current flowing through the electrode (upper curve) caused by charge carriers generated by a radiation particle incident on the diode or the resistor, and a corresponding temporal change of the voltage of the electrode (lower curve). The voltage may be an integral of the electric current with respect to time. At time to, the radiation particle hits the diode or the resistor, charge carriers start being generated in the diode or the resistor, electric current starts to flow through the electrode of the diode or the resistor, and the absolute value of the voltage of the electrode or electrical contact starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the radiation particle drift out of the radiation absorption layer 110. At time $t_s$, the time delay TD1 expires. In the example of FIG. 24, time $t_s$ is after time $t_e$; namely TD1 expires after all charge carriers generated by the radiation particle drift out of the radiation absorption layer 110. The rate of change of the voltage is thus substantially zero at $t_s$. The controller 310 may be configured to deactivate the second voltage comparator 302 at expiration of TD1 or at $t_2$, or any time in between.

The controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment is proportional to the amount of charge carriers generated by a radiation particle, which relates to the energy of the radiation particle. The controller 310 may be configured to determine the energy of the radiation particle based on voltage the voltmeter 306 measures. One way to determine the energy is by binning the voltage. The counter 320 may have a sub-counter for each bin. When the controller 310 determines that the energy of the radiation particle falls in a bin, the controller 310 may cause the number registered in the sub-counter for that bin to increase by one. Therefore, the system 121 may be able to detect a radiation image and may be able to resolve radiation particle energies of each radiation particle.

After TD1 expires, the controller 310 connects the electrode to an electric ground for a reset period RST to allow charge carriers accumulated on the electrode to flow to the ground and reset the voltage. After RST, the system 121 is ready to detect another incident radiation particle. Implicitly, the rate of incident radiation particles the system 121 can handle in the example of FIG. 24 is limited by 1/(TD1+RST). If the first voltage comparator 301 has been deactivated, the controller 310 can activate it at any time before RST expires. If the controller 310 has been deactivated, it may be activated before RST expires.

FIG. 7 schematically shows a temporal change of the electric current flowing through the electrode (upper curve) caused by noise (e.g., dark current, background radiation, scattered radiations, fluorescent radiations, shared charges from adjacent pixels), and a corresponding temporal change of the voltage of the electrode (lower curve), in the system 121 operating in the way shown in FIG. 7. At time t₀, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD1 and the controller 310 may deactivate the first voltage comparator 301 at the beginning of TD1. During TD1 (e.g., at expiration of TD1), the controller 310 activates the second voltage comparator 302. The noise is very unlikely large enough to cause the absolute value of the voltage to exceed the absolute value of V2 during TD1. Therefore, the controller 310 does not cause the number registered by the counter 320 to increase. At time $t_e$, the noise ends. At time $t_s$, the time delay TD1 expires. The controller 310 may be configured to deactivate the second voltage comparator 302 at expiration of TD1. The controller 310 may be configured not to cause the voltmeter 306 to measure the voltage if the absolute value of the voltage does not exceed the absolute value of V2 during TD1. After TD1 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 9:
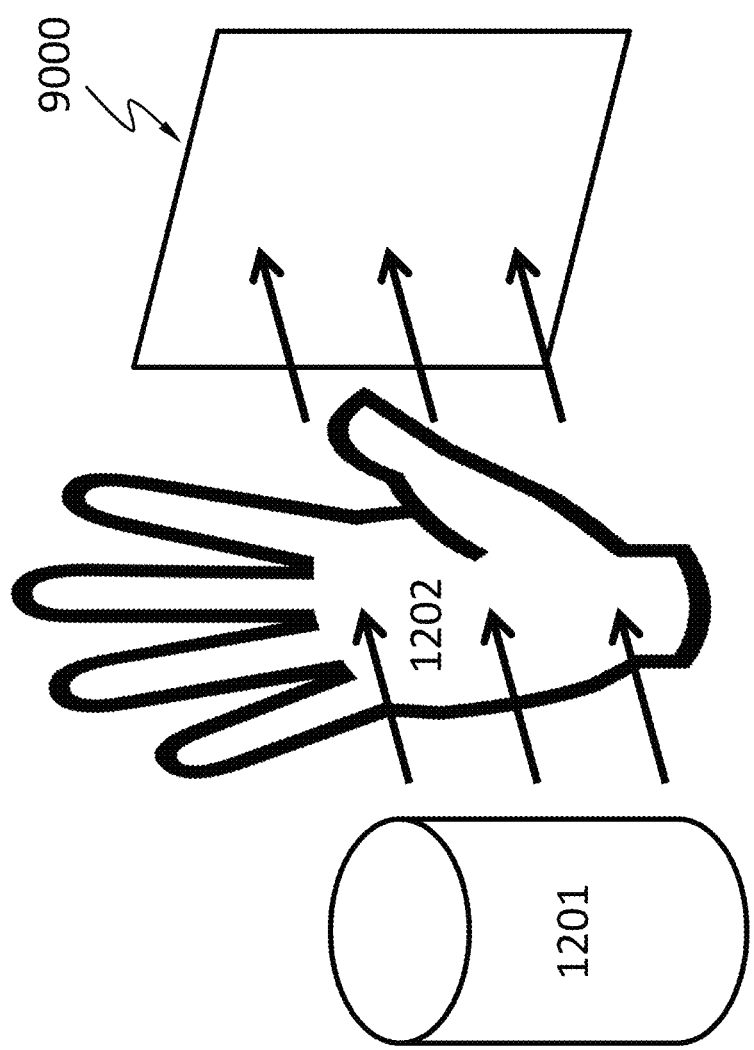
FIG. 9 schematically shows a system comprising the image sensor described herein, suitable for medical imaging such as chest radiography, abdominal radiography, etc., according to an embodiment.

FIG. 9 schematically shows a system comprising an image sensor 9000 as described in relation to FIG. 4A-FIG. 8. The system may be used for medical imaging such as chest radiation radiography, abdominal radiation radiography, etc. The system comprises a radiation source 1201. Radiation emitted from the radiation source 1201 penetrates an object 1202 (e.g., a human body part such as chest, limb, abdomen), is attenuated by different degrees by the internal structures of the object 1202 (e.g., bones, muscle, fat and organs, etc.), and is projected to the image sensor 9000. The image sensor 9000 forms an image by detecting the intensity distribution of the radiation.

Figure 10:
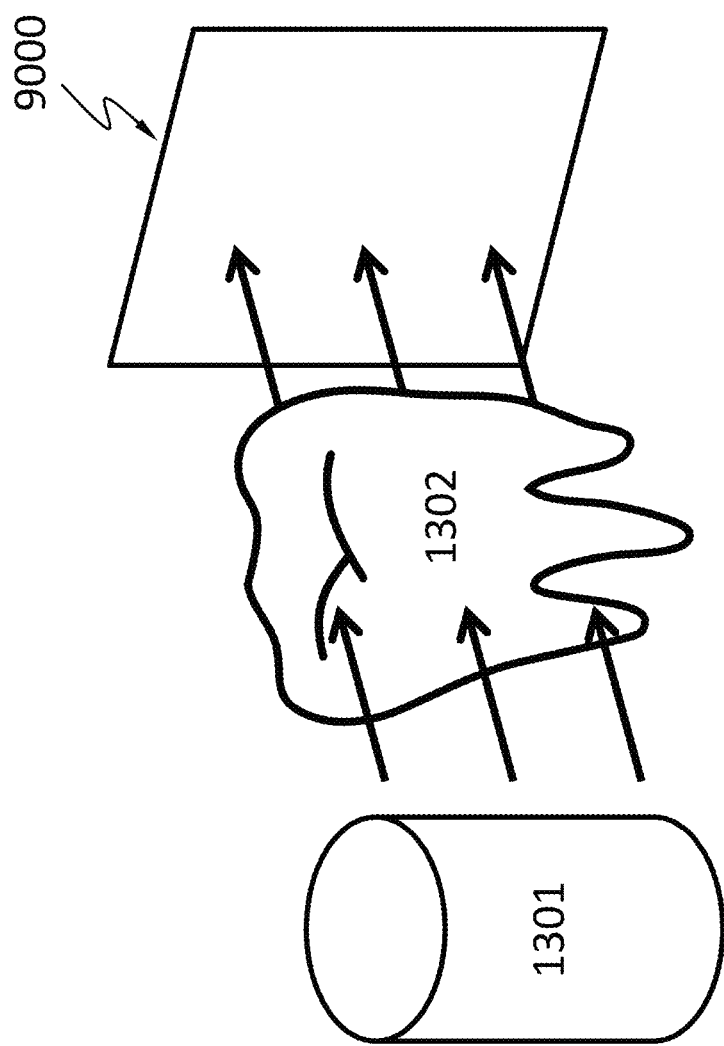
FIG. 10 schematically shows a system comprising the image sensor described herein suitable for dental radiography, according to an embodiment.

FIG. 10 schematically shows a system comprising an image sensor 9000 as described in relation to FIG. 4A-FIG. 8. The system may be used for medical imaging such as dental radiation radiography. The system comprises a radiation source 1301. Radiation emitted from the radiation source 1301 penetrates an object 1302 that is part of a mammal (e.g., human) mouth. The object 1302 may include a maxilla bone, a palate bone, a tooth, the mandible, or the tongue. The radiation is attenuated by different degrees by the different structures of the object 1302 and is projected to the image sensor 9000. The image sensor 9000 forms an image by detecting the intensity distribution of the radiation. Teeth absorb radiation more than dental caries, infections, periodontal ligament. The dosage of radiation received by a dental patient is typically small (around 0.150 mSv for a full mouth series).

Figure 11:
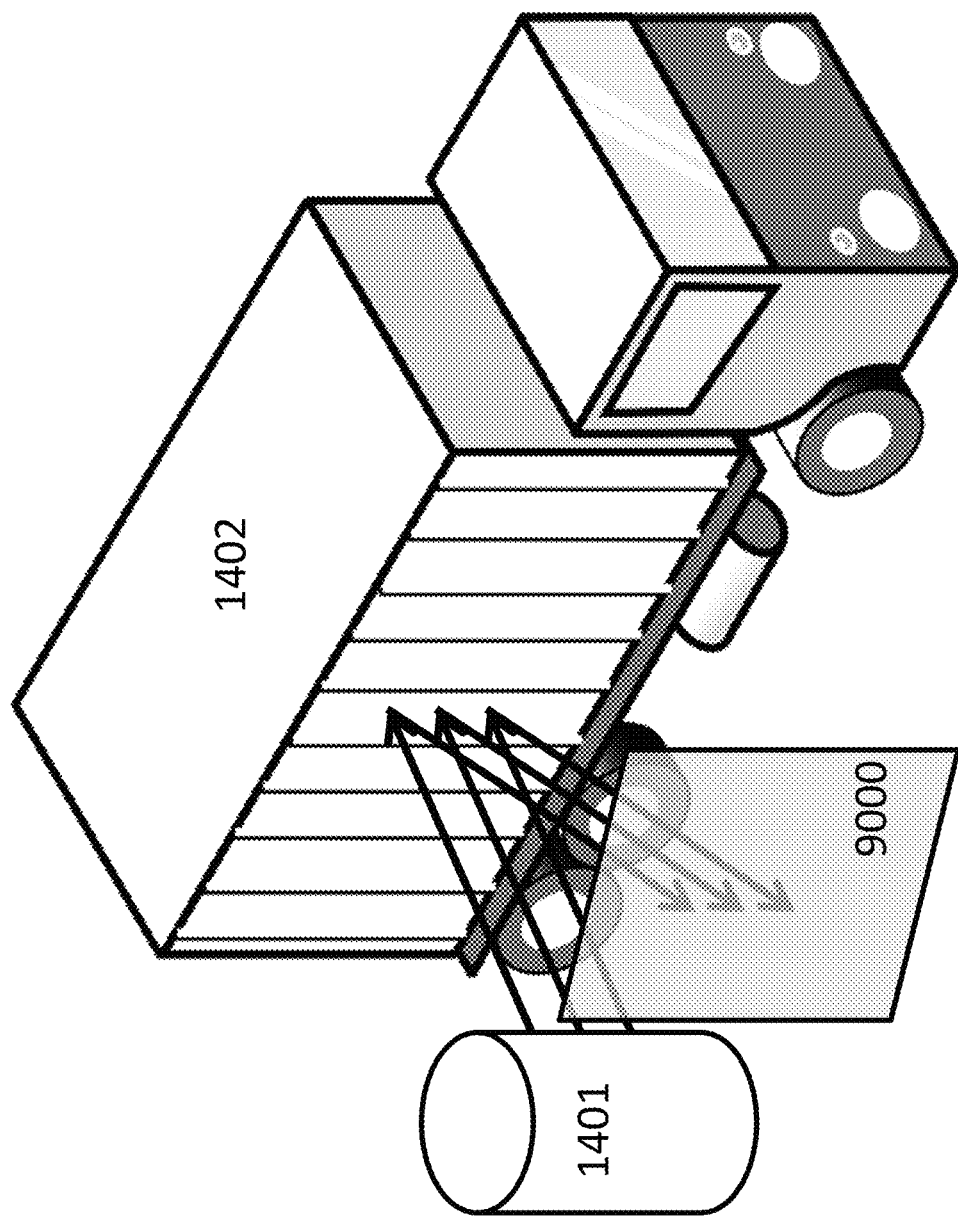
FIG. 11 schematically shows a cargo scanning or non-intrusive inspection (NII) system comprising the image sensor described herein, according to an embodiment.

FIG. 11 schematically shows a cargo scanning or non-intrusive inspection (NII) system comprising an image sensor 9000 as described in relation to FIG. 4A-FIG. 8. The system may be used for inspecting and identifying goods in transportation systems such as shipping containers, vehicles, ships, luggage, etc. The system comprises a radiation source 1401. Radiation emitted from the radiation source 1401 may backscatter from an object 1402 (e.g., shipping containers, vehicles, ships, etc.) and be projected to the image sensor 9000. Different internal structures of the object 1402 may backscatter radiation differently. The image sensor 9000 forms an image by detecting the intensity distribution of the backscattered radiation and/or energies of the backscattered radiation particles.

Figure 12:
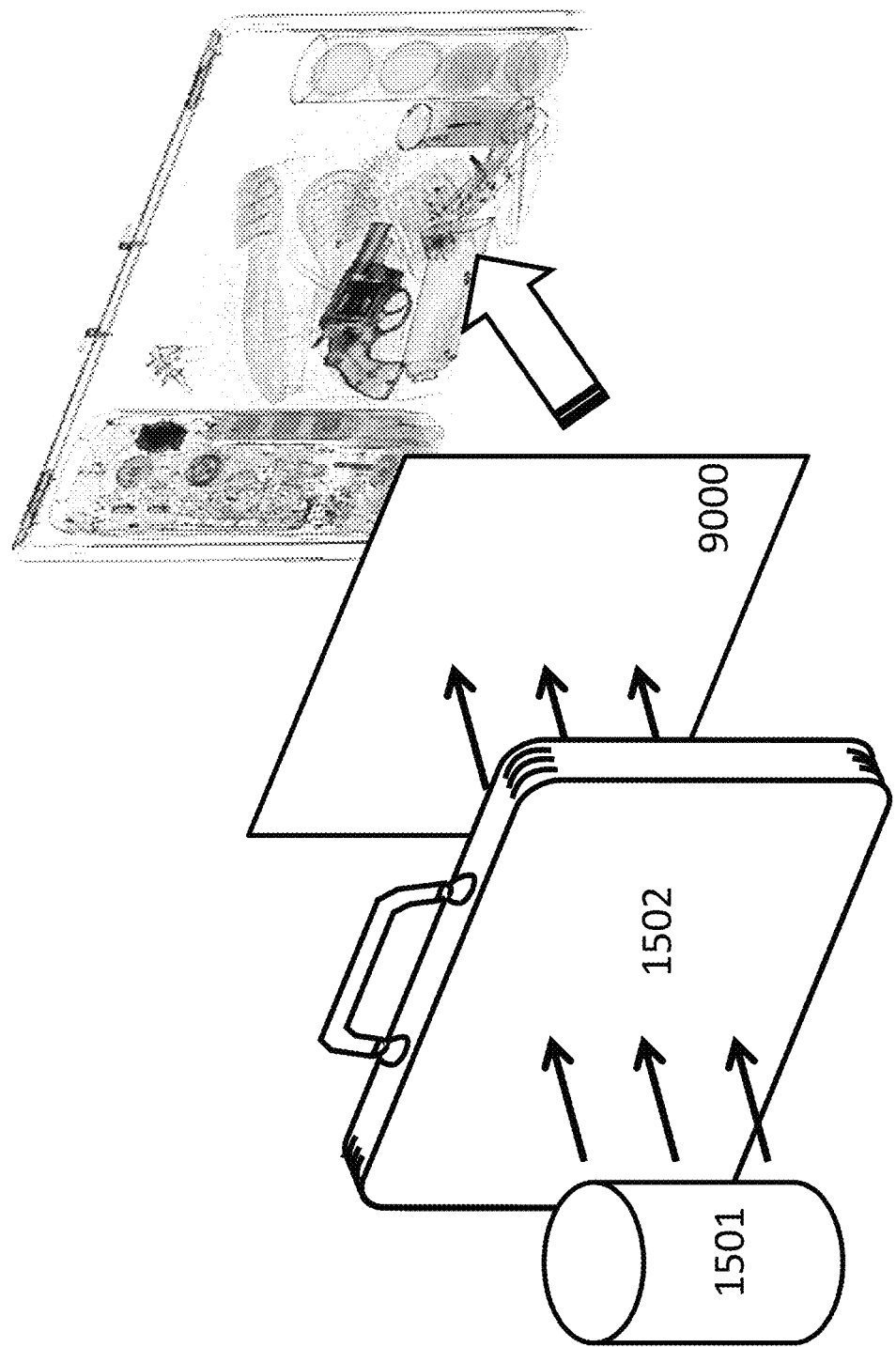
FIG. 12 schematically shows another cargo scanning or non-intrusive inspection (NII) system comprising the image sensor described herein, according to an embodiment.

FIG. 12 schematically shows another cargo scanning or non-intrusive inspection (NII) system comprising an image sensor 9000 as described in relation to FIG. 4A-FIG. 8. The system may be used for luggage screening at public transportation stations and airports. The system comprises a radiation source 1501. Radiation emitted from the radiation source 1501 may penetrate a piece of luggage 1502, be differently attenuated by the contents of the luggage, and projected to the image sensor 9000. The image sensor 9000 forms an image by detecting the intensity distribution of the transmitted radiation. The system may reveal contents of luggage and identify items forbidden on public transportation, such as firearms, narcotics, edged weapons, flammables.

Figure 13:
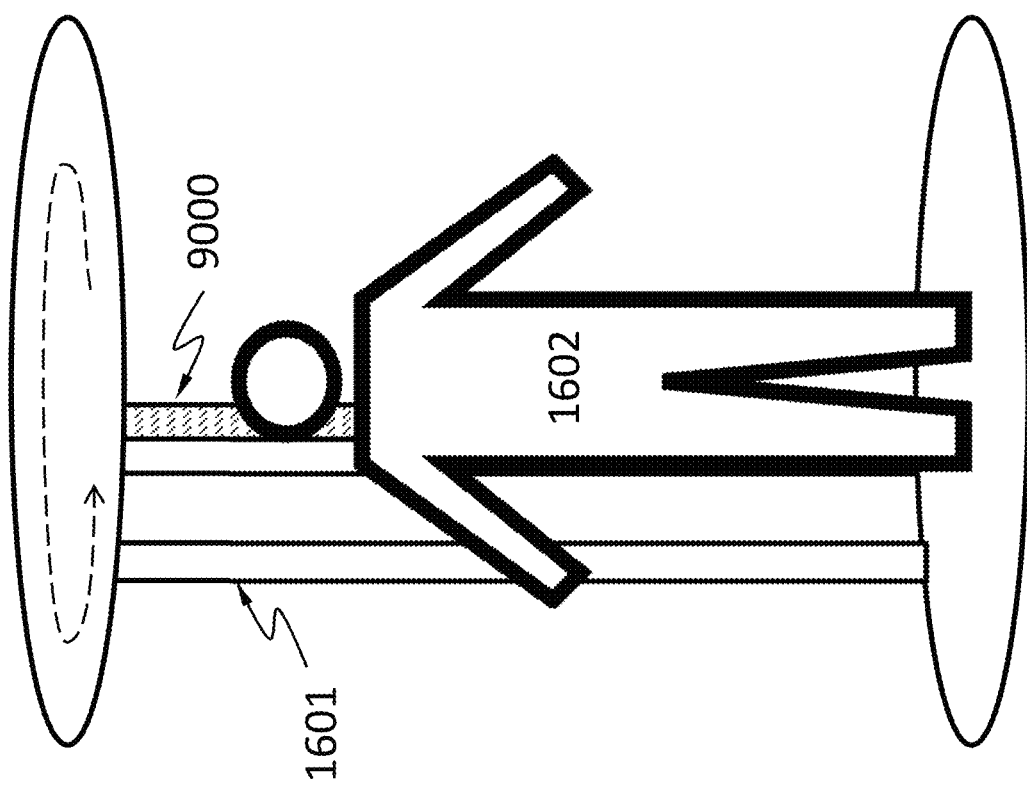
FIG. 13 schematically shows a full-body scanner system comprising the image sensor described herein, according to an embodiment.

FIG. 13 schematically shows a full-body scanner system comprising an image sensor 9000 as described in relation to FIG. 4A-FIG. 8. The full-body scanner system may detect objects on a person's body for security screening purposes, without physically removing clothes or making physical contact. The full-body scanner system may be able to detect non-metal objects. The full-body scanner system comprises a radiation source 1601. Radiation emitted from the radiation source 1601 may backscatter from a human 1602 being screened and objects thereon, and be projected to the image sensor 9000. The objects and the human body may backscatter radiation differently. The image sensor 9000 forms an image by detecting the intensity distribution of the backscattered radiation. The image sensor 9000 and the radiation source 1601 may be configured to scan the human in a linear or rotational direction.

Figure 14:
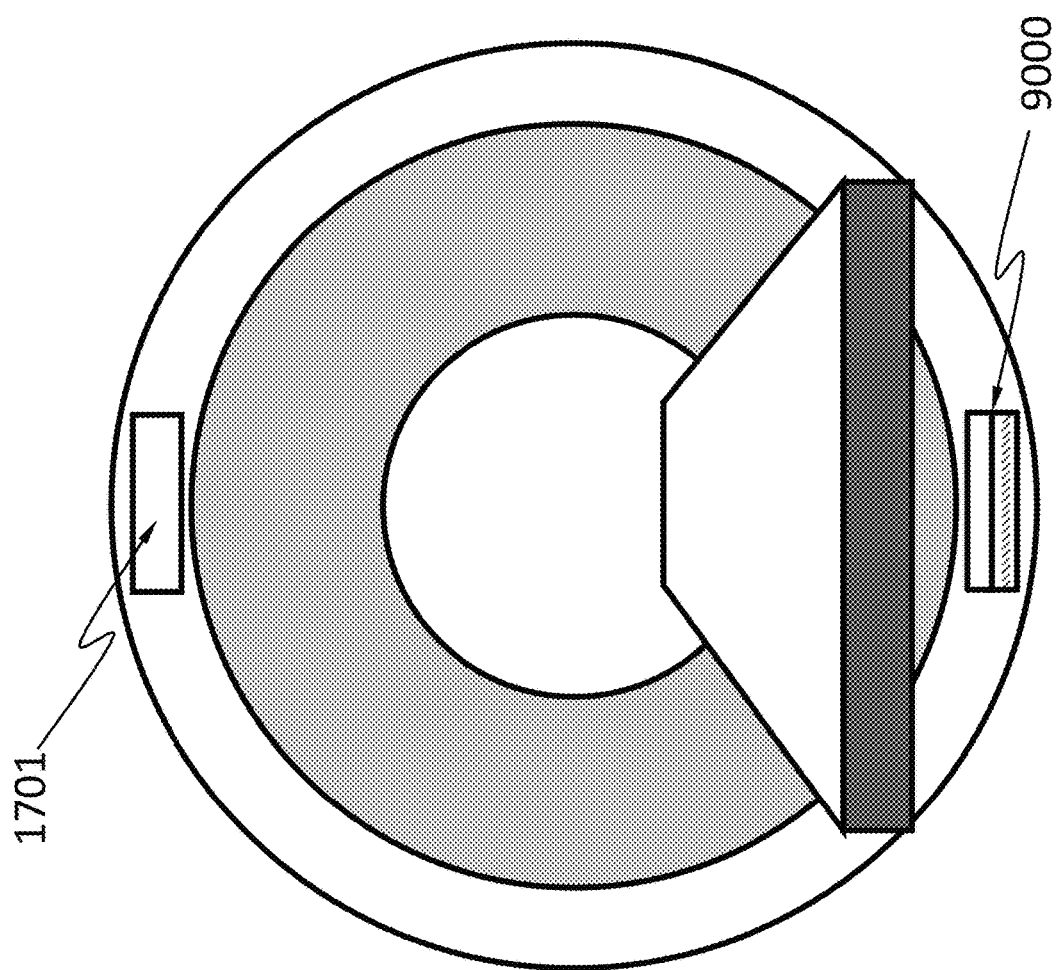
FIG. 14 schematically shows a radiation computed tomography (Radiation CT) system comprising the image sensor described herein, according to an embodiment.

FIG. 14 schematically shows a radiation computed tomography (Radiation CT) system. The Radiation CT system uses computer-processed radiations to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The Radiation CT system comprises an image sensor 9000 as described in relation to FIG. 4A-FIG. 8 and a radiation source 1701. The image sensor 9000 and the radiation source 1701 may be configured to rotate synchronously along one or more circular or spiral paths.

Figure 15:
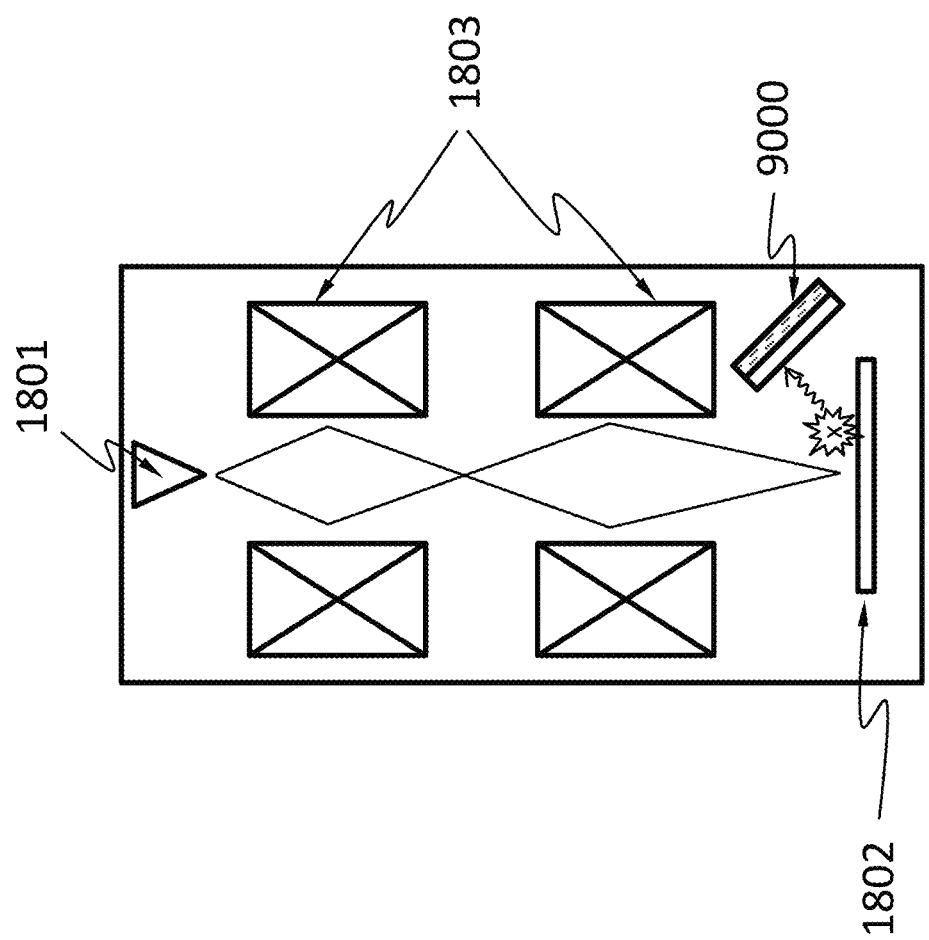
FIG. 15 schematically shows an electron microscope comprising the image sensor described herein, according to an embodiment.

FIG. 15 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise an image sensor 9000 as described in relation to FIG. 4A-FIG. 8, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the image sensor 9000.

The image sensor 9000 described here may have other applications such as in a radiation telescope, radiation mammography, industrial radiation defect detection, radiation microscopy or microradiography, radiation casting inspection, radiation non-destructive testing, radiation weld inspection, radiation digital subtraction angiography, etc. It may be suitable to use this image sensor 9000 in place of a photographic plate, a photographic film, a PSP plate, a radiation image intensifier, a scintillator, or another semiconductor radiation detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An image sensor comprising:
   a first package comprising a plurality of radiation detectors mounted on a printed circuit board (PCB);
   wherein a dead zone of the first package does not extend between neighboring radiation detectors among the plurality of radiation detectors;
   wherein the radiation detectors have no guard rings or sidewall doping;
   wherein each of the radiation detectors comprises an array of pixels;
   wherein pixels on peripheries of the radiation detectors are configured to deduct a contribution of a dark current from energy of a radiation particle incident thereon.

2. The image sensor of claim 1, wherein the first package is mounted on a system PCB by a plug and a receptacle.

3. The image sensor of claim 2, wherein the first package is tilted relative to the system PCB.

4. The image sensor of claim 1, wherein the first package is mounted on a system PCB by wire bonding.

5. The image sensor of claim 1, further comprising a second package, wherein the dead zone of the first package is shadowed by the second package.

6. The image sensor of claim 5, wherein the dead zone of the first package is shadowed by an active area of the second package.

7. The image sensor of claim 1, wherein the first package is rectangular in shape.

8. The image sensor of claim 1, wherein the first package is hexagonal in shape.

9. The image sensor of claim 1, wherein a gap between two neighboring radiation detectors is not wider than a pixel of the two neighboring radiation detectors.

10. The image sensor of claim 1, wherein at least one radiation detector of the radiation detectors does not comprise a perimeter zone along at least three sides of the at least one radiation detector.

11. The image sensor of claim 1, wherein at least one of the radiation detectors comprises a radiation absorption layer and an electronics layer;
    wherein the radiation absorption layer comprises an electrode;
    wherein the electronics layer comprises an electronics system;
    wherein the electronics system comprises:
    a first voltage comparator configured to compare a voltage of the electrode to a first threshold;
    a second voltage comparator configured to compare the voltage to a second threshold;
    a counter configured to register a number of radiation particles reaching the radiation absorption layer;
    a controller;
    wherein the controller is configured to start a time delay from a time at which the first voltage comparator determines that an absolute value of the voltage equals or exceeds an absolute value of the first threshold;
    wherein the controller is configured to activate the second voltage comparator during the time delay;
    wherein the controller is configured to cause the number registered by the counter to increase by one, when the second voltage comparator determines that an absolute value of the voltage equals or exceeds an absolute value of the second threshold.

12. The image sensor of claim 11, wherein the electronics system further comprises a capacitor module electrically connected to the electrode, wherein the capacitor module is configured to collect charge carriers from the electrode.

13. The image sensor of claim 11, wherein the controller is configured to activate the second voltage comparator at a beginning or expiration of the time delay.

14. The image sensor of claim 11, wherein the electronics system further comprises a voltmeter, wherein the controller is configured to cause the voltmeter to measure the voltage upon expiration of the time delay.

15. The image sensor of claim 11, wherein the controller is configured to determine a radiation particle energy based on a value of the voltage measured upon expiration of the time delay.

16. The image sensor of claim 11, wherein the controller is configured to connect the electrode to an electrical ground.

17. The image sensor of claim 11, wherein a rate of change of the voltage is substantially zero at expiration of the time delay.

18. The image sensor of claim 11, wherein a rate of change of the voltage is substantially non-zero at expiration of the time delay.

19. A system comprising the image sensor of claim 1 and a radiation source, wherein the system is configured to perform radiography on human chest or abdomen.

20. A system comprising the image sensor of claim 1 and a radiation source, wherein the system is configured to perform radiography on human mouth.

21. A cargo scanning or non-intrusive inspection (NII) system, comprising the image sensor of claim 1 and a radiation source, wherein the cargo scanning or non-intrusive inspection (NII) system is configured to form an image using backscattered radiation.

22. A cargo scanning or non-intrusive inspection (NII) system, comprising the image sensor of claim 1 and a radiation source, wherein the cargo scanning or non-intrusive inspection (NII) system is configured to form an image using radiation transmitted through an object inspected.

23. A full-body scanner system comprising the image sensor of claim 1 and a radiation source.

24. A radiation computed tomography (Radiation CT) system comprising the image sensor of claim 1 and a radiation source.

25. An electron microscope comprising the image sensor of claim 1, an electron source and an electronic optical system.

26. A system comprising the image sensor of claim 1, wherein the system is a radiation telescope, or a radiation microscopy, or wherein the system is configured to perform mammography, industrial defect detection, microradiography, casting inspection, weld inspection, or digital subtraction angiography.

\* \* \* \* \*